United States Patent
Cai et al.

(10) Patent No.: US 10,562,954 B2
(45) Date of Patent: Feb. 18, 2020

(54) FUSION PROTEIN INHIBITING TACI-BAFF COMPLEX FORMATION AND PREPARATION METHOD THEREFOR AND USE THEREOF

(71) Applicants: Shanghai Kanda Biotechnology Co., Ltd., Shanghai (CN); Shanghai Celgen Bio-Pharmaceutical Co., Ltd., Shanghai (CN)

(72) Inventors: Zeling Cai, Shanghai (CN); Yi Chen, Shanghai (CN); Heng Wu, Shanghai (CN); Guobo Fang, Shanghai (CN)

(73) Assignees: Shanghai Kanda Biotechnology Co., Ltd., Shanghai (CN); Shanghai Celgen Bio-Pharmaceutical Co., Ltd., Shanghai (CN)

( * ) Notice: Subject to any disclaimer, the term of this patent is extended or adjusted under 35 U.S.C. 154(b) by 86 days.

(21) Appl. No.: 15/310,703

(22) PCT Filed: May 12, 2014

(86) PCT No.: PCT/CN2014/077314
§ 371 (c)(1),
(2) Date: Nov. 11, 2016

(87) PCT Pub. No.: WO2015/172305
PCT Pub. Date: Nov. 19, 2015

(65) Prior Publication Data
US 2017/0081387 A1    Mar. 23, 2017

(51) Int. Cl.
| | |
|---|---|
| C07K 14/705 | (2006.01) |
| C07K 14/71 | (2006.01) |
| C07K 14/715 | (2006.01) |
| C07K 14/735 | (2006.01) |
| A61K 38/17 | (2006.01) |
| C12N 15/63 | (2006.01) |
| C12P 21/02 | (2006.01) |
| C07K 19/00 | (2006.01) |
| C07K 16/00 | (2006.01) |
| A61K 38/00 | (2006.01) |
| A61K 39/00 | (2006.01) |

(52) U.S. Cl.
CPC ...... *C07K 14/70578* (2013.01); *A61K 38/179* (2013.01); *A61K 38/1774* (2013.01); *A61K 38/1793* (2013.01); *C07K 14/70535* (2013.01); *C07K 14/70596* (2013.01); *C07K 14/7151* (2013.01); *C07K 16/00* (2013.01); *C07K 19/00* (2013.01); *C12N 15/63* (2013.01); *C12P 21/02* (2013.01); *A61K 38/00* (2013.01); *A61K 38/177* (2013.01); *A61K 2039/505* (2013.01); *C07K 14/705* (2013.01); *C07K 2317/76* (2013.01); *C07K 2319/00* (2013.01); *C07K 2319/03* (2013.01); *C07K 2319/30* (2013.01); *C07K 2319/32* (2013.01)

(58) Field of Classification Search
CPC .............. A61K 38/177; A61K 38/179; A61K 38/1793; C07K 2319/00; C07K 14/70578; C07K 2319/30; C07K 14/705; C07K 14/70596; C07K 14/7151; C07K 2319/32; C07K 19/00
See application file for complete search history.

(56) References Cited

U.S. PATENT DOCUMENTS 8,852,591 B2 * 10/2014 Ponce, Jr. .............. A61K 45/06
                                                                  424/134.1

FOREIGN PATENT DOCUMENTS

| CN | 1980957 A | 6/2007 |
|---|---|---|
| CN | 101160322 A | 4/2008 |
| CN | 103833856 A | 6/2014 |

OTHER PUBLICATIONS

Hu et al. Development of a novel BAFF responsive cell line suitable for detecting bioactive BAFF and neutralizing antibodies against BAFF-pathway inhibiting therapeutics. Cells 3: 79-91, 2014.*
Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Bossen et al. BAFF, APRIL and their receptors: structure, function and signaling. Sem Immunol 18: 263-275, 2006.*
Brenner, S.E. Errors in genome function. Trends in Genetics 15(4): 132-133, 1999.*
Doerks et al. Protein annotation: detective work for function prediction. Trends in Genetics 14(6): 248-250, 1998.*

(Continued)

*Primary Examiner* — Bridget E Bunner
(74) *Attorney, Agent, or Firm* — Wolf, Greenfield & Sack, P.C.

(57) ABSTRACT

The present invention provides a fusion protein inhibiting TACI-BAFF complex formation and preparation method therefor and use thereof. Specifically, the fusion protein of the present invention is of high biological activity for blocking BAFF/APPRIL, and may significantly lower the serum IgM concentration in normal Balb/c mice as well as the serum IgM and IgE concentration in C57/B6 mice with asthma. The TACI-Fc fusion protein of the present invention may be used in the treatment of autoimmune diseases, including asthma, systemic lupus eythematosus and rheumatoid arthritis, etc., and may also be used in the treatment of B cell enrichment-related diseases, including multiple myeloma, chronic lymphocytic leukemia, macroglobulinemia and plasmacytic leukemia, etc.

17 Claims, 7 Drawing Sheets
Specification includes a Sequence Listing.

(56) References Cited

OTHER PUBLICATIONS

Granja et al. Characterization of BAFF and APRIL subfamily receptors in rainbow trout (*Oncorhynchus mykiss*). Potential role of the BAFF/APRIL axis in the pathogenesis of proliferative kidney disease. PLoS One 12(3): e0174249, 2017; 24 total pages.*
Ngo et al. Computational complexity, protein structure prediction, and the Levinthal paradox. The Protein Folding Problem and Tertiary Structure Prediction, pp. 492-495, 1994.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Translation of CN103833856; Apr. 6, 2014; 7 total pages.*
Vanamee et al. Structural principles of tumor necrosis factor superfamily signaling. Sci Signal 11: eaao4910, 2018; 12 total pages.*
Wells. J.A. Additivity of mutational effects in proteins. Biochemistry 29 (37): 8509-8517, 1990.*
Aggarwal, B.B. Signalling pathways of the TNF superfamily: a double-edged sword. Nature Rev Immunol 3(9): 745-756, 2003.*
Hymowitz et al. "Structures of TNF receptors and their interactions with ligands" in Cancer Drug Discovery and Development: Death Receptors in Cancer Therapy. Totowa, NJ: Humana Press, 2005, pp. 65-81.*
Locksley et al. The TNF and TNF receptor superfamilies: integrating mammalian biology. Cell 104: 497-501, 2001.*
Magis et al. An improved understanding of TNFL/TNFR interactions using structure-based classifications. Trends Biochem Sci 37(9): 353-363, 2012.*
Vanamee et al. Structural principles of tumor necrosis factor superfamily signaling. Sci Signaling 11: eaao4910, 2018 (11 total pages).*
Guan et al., Research Advance on the BAFF/APRIL System. Letters in Biotechnology. Mar. 31, 2006;3:394-7.
Guo, Expression, Purification and Bioactivity Identification of TACI-Fc and BCMA-Fc Fusion Proteins. Master's Dissertation of Tianjin University, Aug. 31, 2009 (Abstract only).

* cited by examiner

```
         10         20         30         40         50         60
MSGLGRSRRG GRSRVDQEER FPQGLWTGVA MRSCPEEQYW DPLLGTCMSC KTICNHQSQR 70         80         90        100        110        120
TCAAFCRSLS CRKEQGKFYD HLLRDCISCA SICGQHPKQC AYFCENKLRS PVNLPPELRR 130        140        150        160        170        180
QRSGEVENNS DNSGRYQGLE HRGSEASPAL PGLKLSADQV ALVYSTLGLC LCAVLCCFLV 190        200        210        220        230        240
AVACFIKKRG DPCSCQPRSR PRQSPAKSSQ DHAMEAGSPV STSPEPVETC SFCFPECRAP 250        260        270        280        290
TQESAVTPGT PDPTCAGRWG CHTRTTVLQP CPHIPDSGLG IVCVPAQEGG PGA
```

Figure 1

```
         10         20         30         40         50         60
MAPVAVWAAL AVGLELWAAA HALPAQVAFT PYAPEPGSTC RLREYYDQTA QMCCSKCSPG 70         80         90        100        110        120
QHAKVFCTKT SDTVCDSCED STYTQLWNWV PECLSCGSRC SSDQVETQAC TREQNRICTC 130        140        150        160        170        180
RPGWYCALSK QEGCRLCAPL RKCRPGFGVA RPGTETSDVV CKPCAPGTFS NTTSSTDICR 190        200        210        220        230        240
PHQICNVVAI PGNASMDAVC TSTSPTRSMA PGAVHLPQPV STRSQHTQPT PEPSTAPSTS 250        260        270        280        290        300
FLLPMGPSPP AEGSTGDFAL PVGLIVGVTA LGLLIIGVVN CVIMTQVKKK PLCLQREAKV 310        320        330        340        350        360
PHLPADKARG TQGPEQQHLL ITAPSSSSSS LESSASALDR RAPTRNQPQA PGVEASGAGE 370        380        390        400        410        420
ARASTGSSDS SPGGHGTQVN VTCIVNVCSS SDHSSQCSSQ ASSTMGDTDS SPSESPKDEQ 430        440        450        460
VPFSKEECAF RSQLETPETL LGSTEEKPLP LGVPDAGMKP S
```

Figure 2

```
     216        226         236        246        256        266
EPKSCYKTHT CPPCPAPELL GGPSVFLFPP KPKDTLMISR TPEVTCVVVD VSHEDPEVKF
| ⇐ hinge ⇒ |CH2 ⇒
       region 276        286         296        306        316        326
NWYVDGVEVH NAKTKPREEQ YNSTYRVVSV LTVLHQDWLN GKEYKCKVSN KALPAPIEKT 336        346         356        366        376        386
ISKAKGQPRE PQVYTLPPSR DELTKNQVSL TCLVKGFYPS DIAVEWESNG QPENNYKTTP
⇐CH2 |CH3 ⇒

396        406         416        426        436        446
PVLDSDGSFF LYSKLTVDKS RWQQGNVFSC SVMHEALHNH YTQKSLSLSP GK
                                                       CH3 ⇐ |
```

```
   1 - ATGGCGCCCGTCGCCGTCTGGGCCGCGCTGGCCGTCGGACTGGAGCTCTGGGCTGCGGCG  -  60
   1 - M   A   P   V   A   V   W   A   A   L   A   V   G   L   E   L   W   A   A   A    -  20

61 - CACGCCTTGCCCGCCCAGGTGGCATTTACACCCTACGCCCCGGAGCCCGGGAGCACATGC  - 120
  21 - H   A   L   P   A   Q   V   A   F   T   P   Y   A   P   E   P   G   S   T   C    -  40

121 - CGGCTCAGAGAATACTATGACCAGACAGCTCAGATGTGCTGCAGCAAGTGCTCGCCGGGC  - 180
  41 - R   L   R   E   Y   Y   D   Q   T   A   Q   M   C   C   S   K   C   S   P   G    -  60

181 - CAACATGCAAAAGTCTTCTGTACCAAGACCTCGGACACCGTGTGTGACGCTATGAGATCC  - 240
  61 - Q   H   A   K   V   F   C   T   K   T   S   D   T   V   C   D   A   M   R   S    -  80

241 - TGCCCCGAAGAGCAGTACTGGGATCCTCTGCTGGGTACCTGCATGTCCTGCAAAACCATT  - 300
  81 - C   P   E   E   Q   Y   W   D   P   L   L   G   T   C   M   S   C   K   T   I    - 100

301 - TGCAACCATCAGAGCCAGCGCACCTGTGCAGCCTTCTGCAGGTCACTCAGCTGCCGCAAG  - 360
 101 - C   N   H   Q   S   Q   R   T   C   A   A   F   C   R   S   L   S   C   R   K    - 120

361 - GAGCAAGGCAAGTTCTATGACCATCTCCTGAGGGACTGCATCAGCTGTGCCTCCATCTGT  - 420
 121 - E   Q   G   K   F   Y   D   H   L   L   R   D   C   I   S   C   A   S   I   C    - 140

421 - GGACAGCACCCTAAGCAATGTGCATACTTCTGTGAGAACAAGCTCAGGAGCCCAGTGAAC  - 480
 141 - G   Q   H   P   K   Q   C   A   Y   F   C   E   N   K   L   R   S   P   V   N    - 160

481 - CTTCCACCAGAGCTCAGGGAACCCAAATCTTGTTACAAAACTCACACATGCCCACCGTGC  - 540
 161 - L   P   P   E   L   R   E   P   K   S   C   Y   K   T   H   T   C   P   P   C    - 180

541 - CCAGCACCTGAACTCCTGGGGGGACCGTCAGTCTTCCTCTTCCCCCCAAAACCCAAGGAC  - 600
 181 - P   A   P   E   L   L   G   G   P   S   V   F   L   F   P   P   K   P   K   D    - 200

601 - ACCCTCATGATCTCCCGGACCCCTGAGGTCACATGCGTGGTGGTGGACGTGAGCCACGAA  - 660
 201 - T   L   M   I   S   R   T   P   E   V   T   C   V   V   V   D   V   S   H   E    - 220

661 - GACCCTGAGGTCAAGTTCAACTGGTACGTGGACGGCGTGGAGGTGCATAATGCCAAGACA  - 720
 221 - D   P   E   V   K   F   N   W   Y   V   D   G   V   E   V   H   N   A   K   T    - 240

721 - AAGCCGCGGGAGGAGCAGTACAACAGCACGTACCGTGTGGTCAGCGTCCTCACCGTCCTG  - 780
 241 - K   P   R   E   E   Q   Y   N   S   T   Y   R   V   V   S   V   L   T   V   L    - 260

781 - CACCAGGACTGGCTGAATGGCAAGGAGTACAAGTGCAAGGTCTCCAACAAAGCCCTCCCA  - 840
 261 - H   Q   D   W   L   N   G   K   E   Y   K   C   K   V   S   N   K   A   L   P    - 280

841 - GCCCCCATCGAGAAAACCATCTCCAAAGCCAAAGGGCAGCCCCGAGAACCACAGGTGTAC  - 900
 281 - A   P   I   E   K   T   I   S   K   A   K   G   Q   P   R   E   P   Q   V   Y    - 300

901 - ACCCTGCCCCCATCCCGGGATGAGCTGACCAAGAACCAGGTCAGCCTGACCTGCCTGGTC  - 960
 301 - T   L   P   P   S   R   D   E   L   T   K   N   Q   V   S   L   T   C   L   V    - 320

961 - AAAGGCTTCTATCCCAGCGACATCGCCGTGGAGTGGGAGAGCAATGGGCAGCCGGAGAAC  - 1020
 321 - K   G   F   Y   P   S   D   I   A   V   E   W   E   S   N   G   Q   P   E   N    - 340

1021 - AACTACAAGACCACGCCTCCCGTGCTGGACTCCGACGGCTCCTTCTTCCTCTACAGCAAG  - 1080
 341 - N   Y   K   T   T   P   P   V   L   D   S   D   G   S   F   F   L   Y   S   K    - 360

1081 - CTCACCGTGGACAAGAGCAGGTGGCAGCAGGGGAACGTCTTCTCATGCTCCGTGATGCAT  - 1140
 361 - L   T   V   D   K   S   R   W   Q   Q   G   N   V   F   S   C   S   V   M   H    - 380

1141 - GAGGCTCTGCACAACCACTACACGCAGAAGAGCCTCTCCCTGTCTCCGGGTAAATGA      - 1197
 381 - E   A   L   H   N   H   Y   T   Q   K   S   L   S   L   S   P   G   K   *        - 398
```

Figure 4B

1. Fusion protein A
2. Fusion protein B
3. Marker

FUSION PROTEIN INHIBITING TACI-BAFF COMPLEX FORMATION AND PREPARATION METHOD THEREFOR AND USE THEREOF

RELATED APPLICATIONS

This application is a national stage filing under 35 U.S.C. § 371 of international PCT application PCT/CN2014/077314, filed May 12, 2014, the contents of which are herein incorporated by reference in their entireties.

TECHNICAL FIELD

The present invention relates to biological and pharmaceutical fields and in particular, relates to a fusion protein (e.g., TACI-Fc fusion protein) inhibiting TACI-BAFF complex formation and the preparation therefor and use thereof.

BACKGROUND ART

TNF and receptor superfamily members thereof play an important role in the body in various processes such as defenses, inflammation response, immune regulation and so on. They function through paracrine, autocrine and endocrine in a membrane-bound or soluble form. When they bind to the corresponding receptor, a series of biological effects can be caused.

TNF family receptors typically are type I transmembrane proteins and composed of several extracellular region enriched with cysteine domain (CRD) and an intracellular region comprising TRAF protein connection site, wherein the intracellular region also contains a death domain in some cases.

Human transmembrane activator and calcium modulator and cyclophilin ligand interactor (TACI) belongs to TNFR superfamily and is a type III membrane protein having 293 amino acid residues (166 residues in extracellular domain, 10 residues in transmembrane domain and 117 residues in intracellular function domains), wherein there is no signal peptide in amino-terminal. There are two cysteine-rich repeat regions (S33-66 and C70-C104) in extracellular domain, lacking the "death domain" of TNF family compared to other TNF receptor superfamily members. TACI is mainly expressed on B cells and activated T cells, regulates T-cell non-dependent B-cell antibody response, type transformation and B cell homeostasis, and may have a more important role in the transduction of negative signal.

B lymphocyte stimulator factor (BAFF, also known as BLyS, THANK, zTNF-4, TALL-1 and TNFSF-13B) and A proliferation-inducing factor (APRIL, also known as TALL-2, TRDL-1 and TNFSF-13) are newly discovered two members in TNF ligand superfamily having close relationship and directly related to the development of B lymphocytes, T-cell activation and humoral immunity. The overexpression of BAFF and APRIL may be involved in the production of autoreactive B cell and destruction of autoimmune tolerance, thereby affecting immune response and leading to various autoimmune diseases and malignancies. BAFF can bind to the receptor BCMA (B cell maturation antigen), TACI (TNFR homology transmembrane activator and calcium modulator and cyclophilin ligand interactor) and Hekou BAFF-R (BAFF receptor, BR3), wherein these three receptors are type III transmembrane proteins belonging to TNFR superfamily, and BCMA and TACI are also receptors of APRIL.

TACI is a receptor for both BAFF and APRIL and can recognize BAFF and acts on APPIL. In addition, BAFF/APRRIL heterologous trimer seems to be recognized by TACI.

BAFF/APPRIL, as an important immune regulatory molecule, plays a key role in the maintenance of B cell homeostasis.

BAFF has a strong B cell chemotaxis, can induce activated B cells to secrete large amounts of immunoglobulins such as IgG, IgA, and IgM, etc. to enhance the humoral immune response and can act as a co-stimulating factor regulating T cell activation and response. In the body, it can promote the development of T1-B cells in the spleen into T2-B cells and mature B cells. The overexpression of BAFF may be involved in generation of autoreactive B cells and damage of autoimmune tolerance, i.e., BAFF signal change affects the humoral immune response, thereby resulting in an autoimmune disease or cancer.

The studies have showed that BAFF/APPRIL level is significantly increased in the body of patients suffering autoimmune diseases such as in the serum of patients with systemic lupus erythematosus and the titer of anti-dsDNA antibody thereof is positively correlated. In rheumatoid arthritis patients, serum BAFF/APPRIL level is significantly increased.

Since BAFF/APPRIL overexpression is closely associated with the autoimmune disease, blocking activity of BAFF/APPRIL as a target molecule can reduce the incidence of the disease and reduce the disease symptoms so as to achieve the purpose of mitigation and treatment of autoimmune diseases. The antibodies and corresponding receptors which block BAFF/APPRIL signal can specifically affect the target cells and therefore are potential biological preparation for treating an autoimmune disease.

Therefore, there is an urgent need in the art to develop new compounds which can effectively inhibit or block BAFF/APPRIL pathway.

SUMMARY OF THE INVENTION

The object of the present invention is to provide new compounds which effectively inhibit or block BAFF/APPRIL pathway.

In the first aspect of the present invention, it provides a fusion protein comprising the following elements which are fused together: (a) a TNF receptor or an active fragment thereof; (b) a BAFF receptor or an active fragment thereof, wherein the BAFF receptor (b) includes TACI, BCMA, BAFFR or combinations thereof; and (c) an antibody Fc region;

and the fusion protein has the following features: inhibiting formation of TACI-BAFF complex.

In another preferred embodiment, the fusion protein retains the biological activities of the element (a) and element (b) as described above.

In another preferred embodiment, the fusion protein also has one or more of the following function:
(a) an activity of binding to BAFF;
(b) an activity of binding to TALL-2/APRIL;
(c) lowering concentration of IgE in serum;
(d) lowering concentration of immunoglobulin, such as IgM, etc. in serum;
(e) decreasing weight of spleen;
(f) inhibiting or blocking BAFF/APPRIL pathway;
(g) reducing number of B cells.

In another preferred embodiment, the fusion protein has the structure as shown in the following Formula I or II:

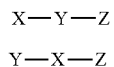

wherein,

X is the first domain of extracellular region of TNF receptor, or an extracellular region of TNF receptor containing the first domain (e.g., the first to second domains, the first to third domains and the first to fourth domains);

Y is a full-length extracellular region of TACI, BCMA or BAFFR, or is a TACI extracellular region containing at least amino acids at Position 30 to 119;

Z is absent, or optionally an Fc region of human antibody; represents a peptide bond or a peptide linker.

In another preferred embodiment, any two of X, Y and Z are connected in a head-head, head-tail, or tail-tail manner.

In another preferred embodiment, the "head" refers to the N-terminal of polypeptide or fragment thereof, and especially the N-terminal of wild-type polypeptide or fragment thereof.

In another preferred embodiment, the "tail" refers to the C-terminal of polypeptide or fragment thereof, and especially the C-terminal of wild-type polypeptide or fragment thereof.

In another preferred embodiment, the peptide linker is a peptide linker having a length of 1 to 20aa.

X contains or has an amino acid sequence of Position 23-76, 23-118, 23-162, or 23-201 of TNF-R2, and/or Y contains or has an amino acid sequence of Position 30-119 of TACI, and/or an amino acid sequence of Position 1-54 of BAFF receptor BCMA, and/or an amino acid sequence of Position 1-78 of BAFF receptor BAFFR.

In another preferred embodiment, Z contains or has an amino acid sequence of Position 216-447 of human γ1.

In another preferred embodiment, the fusion protein has an amino acid sequence of Position 1-398, 23-398, or 39-398 in SEQ ID NO.: 5.

In the second aspect of the present invention, it provides a nucleic acid molecule encoding any one of the fusion proteins in the first aspect of the present invention.

In another preferred embodiment, the nucleic acid molecule has a nucleotide sequence of position 1-1197, 67-1197 or 115-1197 as shown in SEQ ID NO.: 4.

In the third aspect of the present invention, it provides a vector containing the nucleic acid molecule in the second aspect of the present invention.

In the fourth aspect of the present invention, it provides a genetically engineered cell, wherein the cell contains the vector in the third aspect of the present invention; or the nucleic acid molecule in the second aspect of the present invention is integrated into the genome of the cell.

In the fifth aspect of the present invention, it provides a method for producing the fusion protein of the present invention, which comprises the steps of:

culturing the host cell in the fourth aspect of the invention under condition suitable for expressing the fusion protein thereby expressing the fusion protein; and isolating or purifying the fusion protein.

In the sixth aspect of the present invention, it provides a pharmaceutical composition, which comprises the fusion protein of the present invention and a pharmaceutically acceptable carrier.

In the seventh aspect of the present invention, it provides a use of the fusion protein of the present invention for preparation of one or more compositions selected from the group consisting of: (a) a composition for inhibiting BAFF/APPRIL signaling pathway; (b) a composition for reducing IgE, IgM concentration in serum or blood; (c) a composition for treating immune disease; and (d) a composition for treating B-cell increasement-related disease.

In another preferred embodiment, the composition is a pharmaceutical composition.

In another preferred embodiment, the immune disease includes asthma, systemic lupus erythematosus, rheumatoid arthritis and so on.

In another preferred embodiment, the B cell increasement-related disease includes multiple myeloma, chronic lymphocytic leukemia, macroglobulinemia and plasma cell leukemia.

In another preferred embodiment, the composition is also used to reduce weight of spleen.

In the eighth aspect of the present invention, it provides a method for (a) reducing IgE and/or IgM concentration in blood or serum; (c) for treating immune disease or (d) treating B cell increasement-related disease, wherein the method comprises the step of: administering the fusion protein in the first aspect of the present invention to a subject in need.

It should be understood that within the scope of the present invention, any of the technical features specifically described above and below (such as the Examples) can be combined with other technical features, thereby constituting a new or preferred technical solution which needs not be described one by one.

BRIEF DESCRIPTION OF DRAWINGS

FIG. 1 shows the amino acid sequence of human TACI (SEQ ID NO.: 1). The Italics portion represents two cysteine-rich domain (Cysteine-Rich Domain, CRD). The portion labeled in box is a transmembrane sequence. The underlined portion is main stem sequence.

FIG. 2 shows the amino acid sequence of human TNF-R2 (SEQ ID NO.: 2). The underlined sequence is the first cysteine-rich domain. The portion labeled in box is a transmembrane sequence.

FIG. 4B shows the nucleotide sequence encoding fusion protein A precursor (SEQ ID NO.: 4) and its encoded amino acid sequence (SEQ ID NO.: 5), wherein the elements are as follows:

TNF-R2 element: nucleotide sequence: Position 67-228; amino acid sequence: Position 23-76, wherein the cysteine-rich domain CRD1 is located at Position 115-228 in the nucleotide sequence; amino acid sequence is located at Position 39-76;

TACI element: nucleotide sequence: Position 229-498; amino acid sequence: Position 77-166;

Fc region element: nucleotide sequence: Position 499-1194; amino acid sequence: Position 167-398.

In addition, amino acids at position 1-22 of fusion protein A precursor are also from amino acids at position 1-22 of TNF-R2. This amino acid sequence is a transmembrane signal peptide, which is cut off when the protein passes through the membrane and is secreted extracellularly. Therefore, the mature fusion protein does not contain this amino acid sequence.

Figure 5:
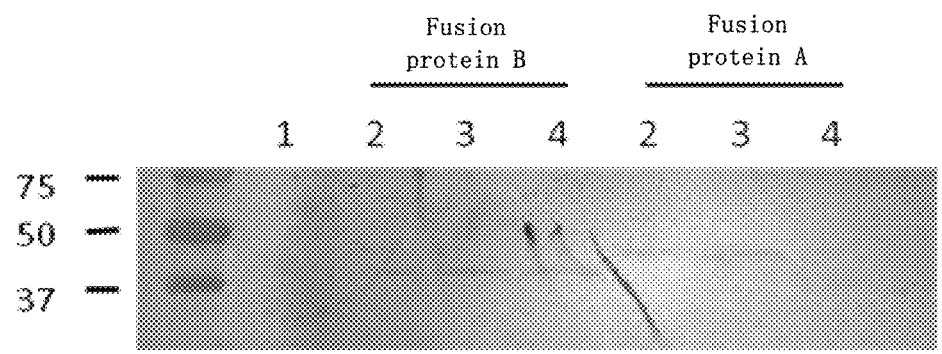

FIG. 5 shows a Western Blot detection of transient expression of the fusion protein in transfected cells. The developing agent is alkaline phosphatase labeled anti-human Fc antibody. The lanes are as follows: 1. the cell culture medium without transfection; 2. transfection with 1 μg Plasmid DNA; 3. transfection with 2 μg DNA plasmid; 4. transfection with 4 μg DNA plasmid.

Figure 6:
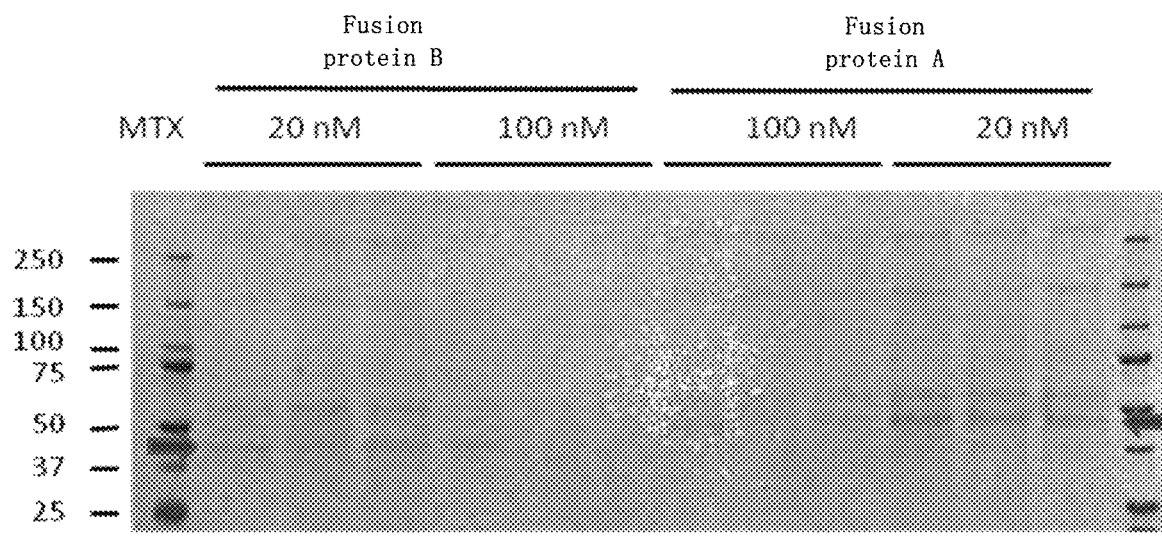

FIG. 6 shows the SDS-PAGE analysis of the expression amount of the fusion protein. After the cells were cultured in 96-well plate for 13 days, 20 μl culture medium was removed and separated by SDS-PAGE. Coomassie Blue was used for developing. The expressed fusion proteins were marked with arrows.

Figure 7:
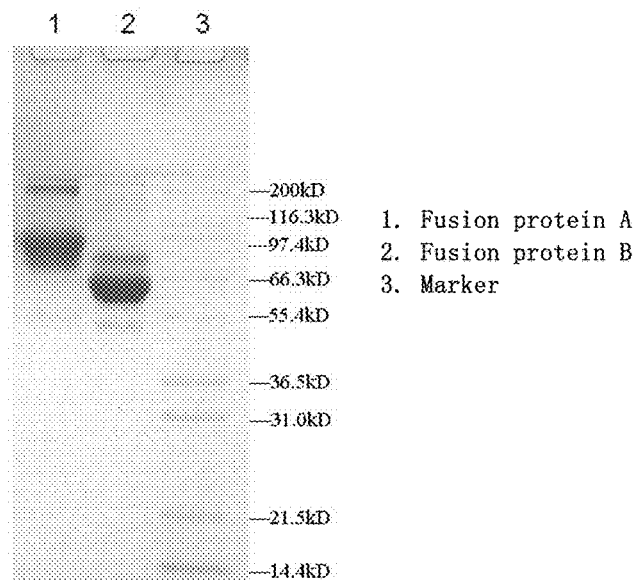

FIG. 7 shows non-reductive electrophoretogram of the fusion proteins A and B after a four-step separation and purification.

Figure 8:
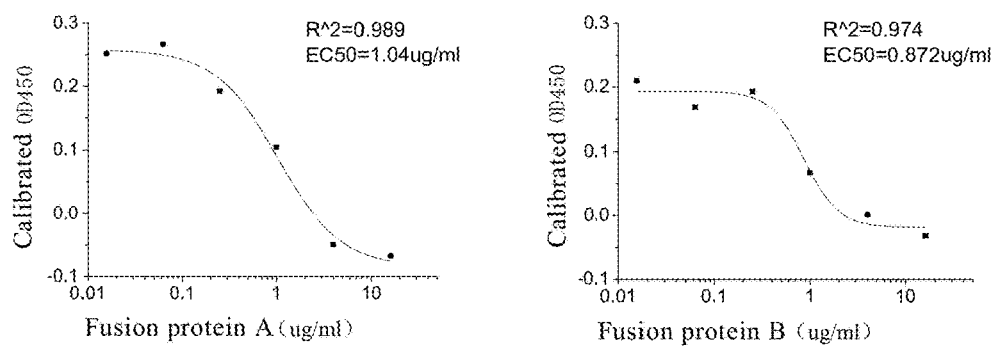

FIG. 8 shows the effect of fusion proteins A and B on RPMI 8226 cells proliferation. Figure A shows the comparison of cell activity of fusion protein A and fusion protein B while Figure B shows the comparison of cell activity of fusion proteins A and TACI-Fc (R&D).

Figure 9:
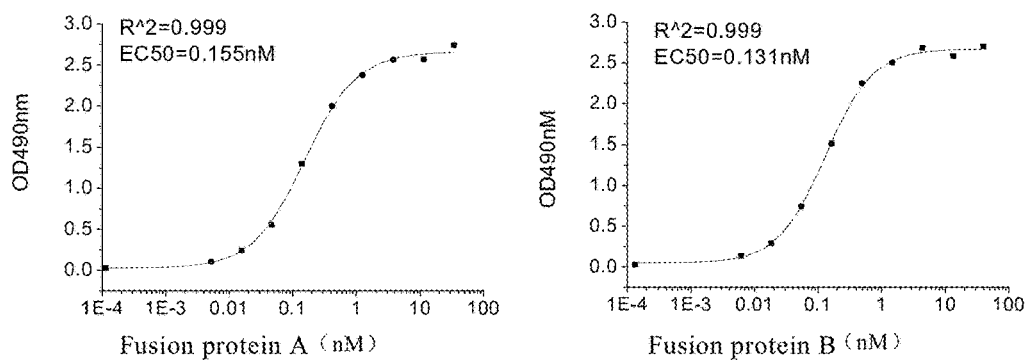

FIG. 9 shows the binding assay in vitro of fusion proteins A and B with rhBAFF. The results showed that the fusion protein retained binding activity of TACI and ligand thereof.

Figure 10:
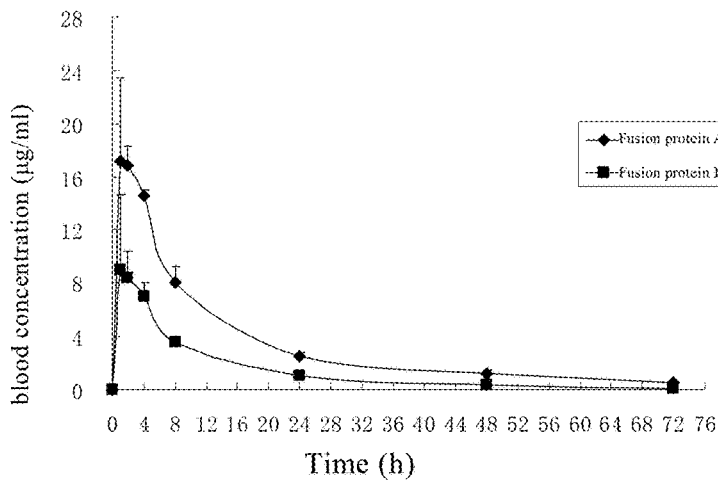

FIG. 10 shows a blood concentration versus time curve after a single dose of the fusion protein A or fusion protein B. The results showed that the half-life of fusion protein was increased, and plasma concentration was significantly increased.

Figure 11:
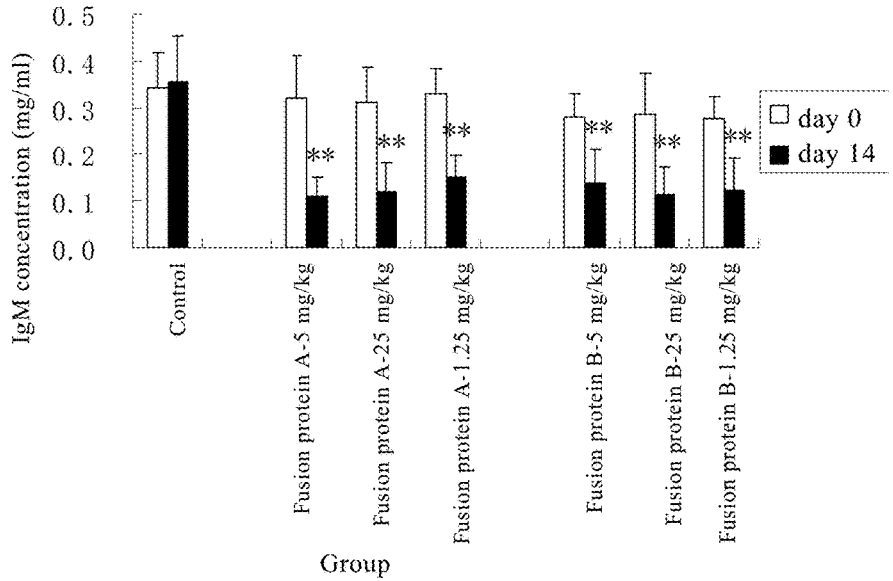

FIG. 11 shows the effects of different doses of the fusion proteins A and B on IgM concentration in serum of normal BALB/C mice.

Figure 12:
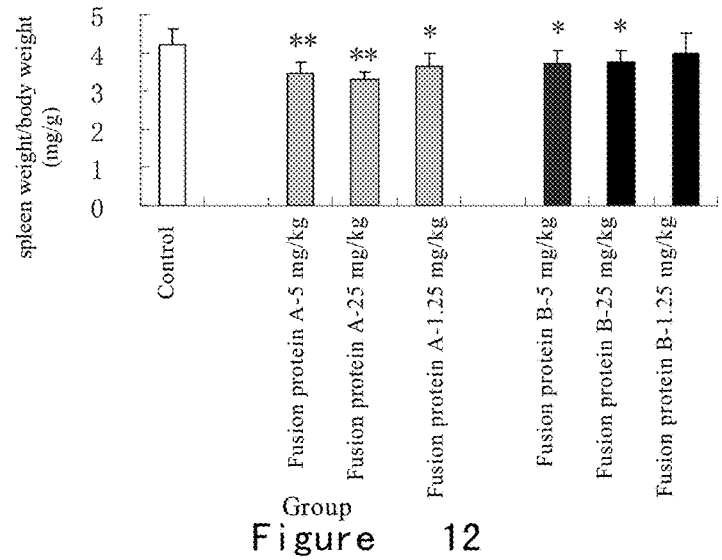

FIG. 12 shows the effects of different doses of the fusion proteins A and B on spleen weight/body weight of normal BALB/C mice.

Figure 13:
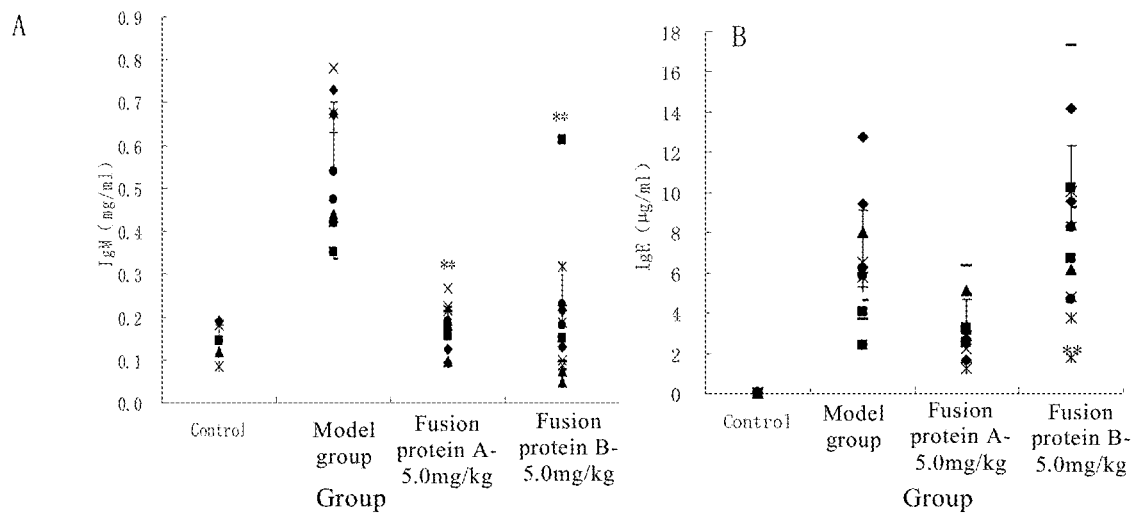

FIG. 13 shows the effects of the fusion proteins A and B on IgE (panel B) and IgM (panel A) concentrations in serum of C57/B6 mice with asthma induced by OVA.

Figure 14:
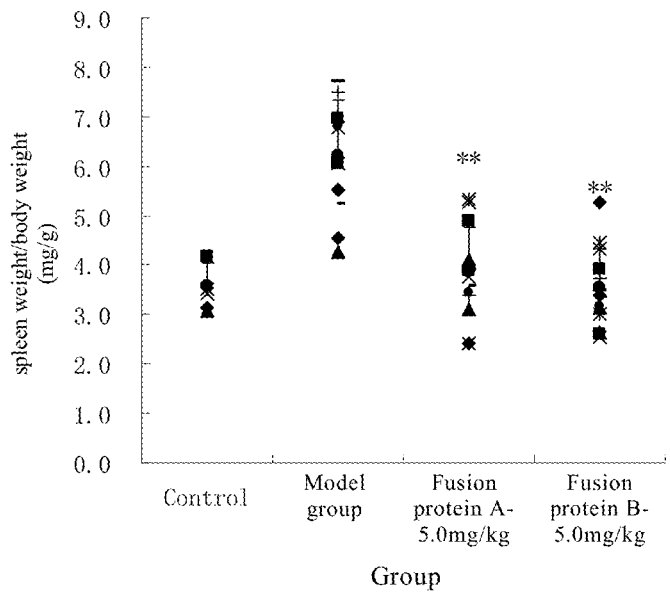

FIG. 14 shows the effects of the fusion proteins A and B on spleen weight/body weight of C57/B6 mice with asthma induced by OVA.

DETAILED DESCRIPTION

After the intensive studies, the present inventors have unexpectedly found that when (a) TNF receptor or active fragments thereof, (b) TACI, BCMA, BAFFR or active fragments thereof, and (c) an antibody Fc region are fused, a fusion protein is obtained which has extremely high biological activity, and concentrations of IgE in serum can be very significantly reduced. In addition, the fusion protein has good stability and long half-life, thus helping to treat certain autoimmune diseases. On this basis, the present invention was completed.

In particular, the present inventors have prepared an optimized TACI-Fc fusion protein. The studies have shown that the fusion protein has a strong biological activity and significantly reduces IgM concentration in serum and spleen weight of normal Balb/c mice. Furthermore, the fusion protein of the present invention can significantly reduce IgE concentration in serum of C57/B6 mice with asthma, thus establishing a foundation for preparation of TACI-Fc fusion protein and its use in treatment of diseases.

As used herein, unless otherwise indicated, TNF-R2, TNFR II, and hTNFR II can be used interchangeably and all refer to human tumor necrosis factor receptor II.

As used herein, unless otherwise indicated, Fc refers to an Fc fragment of human immunoglobulin. The term "immunoglobulin Fc region" refers to a constant region of immunoglobulin chain, and particularly the carboxy terminus or a part of constant region of immunoglobulin heavy chain. For example, the immunoglobulin Fc region may comprise a combination of an immunoglobulin hinge region and two or more domains from heavy chain CH1, CH2, and CH3. In a preferred embodiment, the useful immunoglobulin Fc region comprises at least one immunoglobulin hinge region, a CH2 domain and a CH3 domain, and preferably lacks CH1 domain.

A variety of human immunoglobulin classes, such as IgA, IgD, IgE, IgM and IgG (including four subclasses: IgG1, IgG2, IgG3, IgG4) have been known. It is well known by the skilled in the art to select a specific immunoglobulin Fc region from specific immunoglobulin classes and subclasses. In a preferred embodiment, the immunoglobulin Fc region containing the coded sequence of Fc region of human immunoglobulin subclass IgG4 can be selected, wherein the coded sequence of immunoglobulin heavy chain 1 domain (CH1) is missing and the coded sequences of hinge region, and two domains of CH2 and CH3 are included.

As used herein, unless otherwise indicated, the terms "contain", "have" or "include" include "comprise", "essentially consist of", "substantially consist of", and "consist of". The terms of "essentially consist of", "substantially consist of" and "consist of" belong to the specific terms of "contain", "have" or "include".

As used herein, unless otherwise noted, the fusion protein is an isolated protein which has no association with other proteins, polypeptides or molecules and is a purified product from recombinant host cell culture or as a purified extract.

The present invention provides a fusion protein, comprising the following elements: (a) a TNF receptor or active fragment thereof, (b) a BAFF receptor (e.g., TACI, BCMA and BAFFR is) or active fragment thereof, and (c) an antibody Fc region. In the fusion protein according to the present invention, a linker sequence may or may not be contained among elements (e.g. between element a and element b, or between element b and element c). The linker sequence typically does not affect two partner proteins.

The fusion proteins of the present invention not only has a longer half-life in vivo, but also can more effectively suppress the concentration of immune disease-associated antibody (especially IgE) in serum.

According to the amino acid sequences of the present invention, the skilled in the art can easily prepare the fusion proteins of the present invention by using various known methods. These methods include such as, but are not limited to: recombinant DNA method, synthetic method, etc. [see Murray K M, Dahl S L Ann; Pharmacother 1997 November; 31 (11): 1335-8].

After learning the amino acid sequence of the fusion protein of the present invention, the skilled person can easily obtain gene sequence encoding the fusion protein of the present invention according to the amino acid sequences.

As a preferred embodiment of the present invention, the encoding gene of the fusion protein of the present invention has a sequence as shown in SEQ ID NO: 4. This sequence is especially suitable to highly express the fusion proteins of the present invention in eukaryotic cells (preferably CHO cells), wherein the amino acid sequence thereof includes e.g., a full length sequence of SEQ ID NO.: 5 (i.e., Position 1-398) or active fragment thereof, a polypeptide (fusion protein) as shown in Position 23-398 or Position 39-398.

Based on the nucleotide sequences described herein, the skilled in the art can easily prepare the encoding nucleic acid of the present invention by using a variety of known methods. These methods include, for example, but are not limited to, PCR, DNA synthetic methods. The specific methods can be found in J. Sambrook, "Molecular Cloning, A Laboratory Manual." As an embodiment of the present invention, the encoding nucleic acid sequences of the present invention can be constructed by using a segmented synthesis followed by overlap extension PCR amplification.

The present invention also provides an expression vector containing the sequence of the fusion protein of the present invention and a expression control sequence operably linked thereto. Said "operably linked" or "operably linked to" refers to a situation, i.e., certain portions of a linear DNA sequence can regulate or control the activity of other portions of the same linear DNA sequence. For example, if the promoter can control the transcription of the sequence, then it is operably linked to the coding sequence.

Expression and cloning vectors may contain one or more selection gene, also known as selectable marker. A typical screening protein encoded by a gene can (a) resist antibiotics, etc; (b) compensate nutritional deficiencies or (c) provide key nutriment that is not present in the medium. For example, DHFR (dihydrofolate reductase deficient cell)-deficient DG44 cells can not grow in medium without hypoxanthine-thymine. After the cells is transfected with vectors expressing DHFR, the transfected cells can grow in medium without hypoxanthine-thymine, and also can grow in medium containing a certain amount of MTX (methotrexate).

Expression vector and cloning vector usually contain one or more of gene transcription promoter, or can be identified by prokaryotic cell transcriptional mechanism or identified by eukaryotic cell transcriptional mechanism. The promoter used for eukaryotic cell transcription includes but is not limited to, cytomegalovirus (CMV) promoter, retrovirus promoter, simian virus 40 (SV40) pre-promoter and so on.

The expression vector may be commercially available. It includes, for example, but is not limited to: pIRES, pDR, pUC18, etc. which can be used as a vector for expression in eukaryotic cell system. The skilled in the art can select suitable expression vectors according to the host cell.

According to the known restriction map of no-load expression vector, one skilled in the art can insert the coding sequence for the fusion protein of invention into an appropriate restriction site by restriction enzyme cleavage and splicing in accordance with conventional method to obtain the recombinant expression vector of the present invention.

The present invention also provides a host cell expressing the fusion protein of the present invention, in which the coding sequence of the fusion protein of the present invention is contained. The host cell is preferably an eukaryotic cell, such as but is not limited to CHO, COS cell, 293 cell, RSF cell and the like. As a preferred embodiment of the present invention, the cells are CHO cells, which can express the fusion protein of the present, and the fusion protein with good binding activity and good stability can be obtained.

The present invention also provides a method for preparing the fusion protein of the present invention by using recombinant DNA, comprises the steps of:

1) providing a nucleic acid sequence encoding the fusion protein (e.g., sequence of SEQ ID NO: 4);

2) inserting the nucleic acid sequence of 1) into an appropriate expression vector, thereby obtaining a recombinant expression vector;

3) introducing the recombinant expression vector of 2) into a suitable host cell;

4) culturing the transformed host cell under a condition suitable for expression;

5) collecting the supernatant and purifying the fusion protein product.

The coding sequence can be introduced into the host cell by using a variety of techniques known in the art, which include such as, but are not limited to: calcium phosphate precipitation, protoplast fusion, lipofection, electroporation, microinjection, reverse transcription method, phage transduction method, and alkali metal ion method.

Culturing and the expression of host cells can be found in Olander R M Dev Biol Stand 1996: 86: 338. The cells and residues in suspension can be removed by centrifugation and then the supernatant is collected. It can be identified by polyacrylamide gel electrophoresis.

The fusion protein prepared as described above may be purified to obtain substantially uniform properties, for example a single band is present in SDS-PAGE electrophoresis. For example, when the recombinant protein is secreted and expressed, the protein can be separated by commercially available ultrafiltration membrane, such as the products from Millipore and Pellicon, etc. The expression supernatant is concentrated at first. The concentrated liquid can be further purified using gel chromatography or ion exchange chromatography, e.g., anion exchange chromatography (DEAE, etc.) or cation exchange chromatography. Gel matrix may be polyacrylamide, dextran, polyamide and the like which are commonly used as protein purification matrix. Q- or SP-group is an ideal ion exchange group. Finally, the above purified product can be further refined and purified by hydroxyapatite adsorption chromatography, metal chelate chromatography, hydrophobic interaction chromatography and reverse phase high performance liquid chromatography (RP-HPLC). All of the above purification steps can be used in different combinations, so that the final protein purity is substantially uniform.

The expressed fusion protein can be purified using affinity column containing specific antibody, receptor or ligand for the fusion protein. According to the characteristics of the affinity column used, conventional methods, such as high-salt buffer, pH changes and other methods can be used to elute the fusion polypeptide bound in the affinity column. Alternatively, amino or carboxy terminus of the fusion protein may also contain one or more polypeptide fragments as a protein tag. Any suitable label can be used in the present invention. For example, the label may be a FLAG, HA, HAL c-Myc, 6-His, 8-His or the like. These tags can be used for fusion protein purification.

The present invention also provides a composition comprising an effective amount (e.g. 0.000001-90 wt %; preferably 0.1-50 wt %; more preferably, 5-40 wt %) of the fusion proteins of the present invention, and a pharmaceutically acceptable carrier.

Typically, the fusion protein of the present invention may be formulated in a non-toxic, inert and pharmaceutically acceptable aqueous carrier medium, wherein the pH is typically about 5-8, and preferably, pH is about 6-8.

As used herein, the term "effective amount" or "effective dosage" refers to the amount which can achieve function or activity in human and/or animal and is acceptable by human and/or animal.

As used herein, "pharmaceutically acceptable" component is a substance which is suitable for human and/or mammal without undue adverse side effects (such as toxicity, stimulation and allergy) with a reasonable benefit/risk ratio. The term "pharmaceutically acceptable carrier" refers to a carrier for administration of a therapeutic agent including various excipients and diluents.

The pharmaceutical composition of the present invention comprises a safe and effective amount of the fusion protein of the present invention and a pharmaceutically acceptable carrier. Such carriers include, but are not limited to, saline, buffer solution, dextrose, water, glycerol, ethanol, and combinations thereof. In general, the pharmaceutical preparation should match the mode of administration. The pharmaceutical composition of the present invention can be formulated into the form of injection, such as with saline or an aqueous solution containing glucose and other adjuvants by using conventional methods. The pharmaceutical composition is preferably produced under sterile conditions. The dose of the active ingredient is a therapeutically effective amount. The pharmaceutical formulations of the present invention may also be formulated as a sustained release preparation.

The effective amount of the fusion protein of the present invention may vary depending on the mode of administration and the severity of the disease to be treated. The selection of preferred effective amount can be determined depending on various factors by those skilled in the art (e.g., via clinical trials). The factors include, but are not limited to: the pharmacokinetic parameters of the fusion protein such as bioavailability, metabolism, half-life and the like; the severity of the patient's disease to be treated, the weight of the patient, the immune status of the patient, administration way and the like. Typically, when the fusion protein of the present invention is administered at a dose of about 0.00001 mg-50 mg/kg animal body weight (preferably 0.0001 mg-10 mg/kg animal body weight), the satisfactory results can be obtained. For example, according to the urgent requirements of the treatment status, several divided doses can be administered daily, or the dosage can be reduced proportionally.

The main advantages of the present invention include:

(a) the fusion protein of the present invention has a long half-life;

(b) the fusion protein of the present invention can significantly reduce concentration of IgE in serum;

(c) the fusion protein of the present invention can specifically inhibit the formation of TACI-BAFF complex, thereby terminating the activation of TACI on membrane, thereby terminating signaling transduction.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (New York: Cold Spring Harbor Laboratory Press, 1989) or as instructed by the manufacturer. Unless otherwise specified, all percentages, ratios, proportions or parts are by weight.

Example 1

Construction of Plasmid Expressing Fusion Protein A

A precursor of the fusion protein A (FIG. 4) was composed of the following three fragments from N-terminus to C-terminus, and the specific amino acid sequences were as follows.

Fragment 1. Position 1-76 of TNF-R2 amino acid sequence, comprising the first cysteine-rich domain (FIG. 2).

Fragment 2. Position 30-119 of TACI amino acid sequence, comprising two cysteine-rich domains and partial main stem sequence (FIG. 1).

Figures 3, 4A:
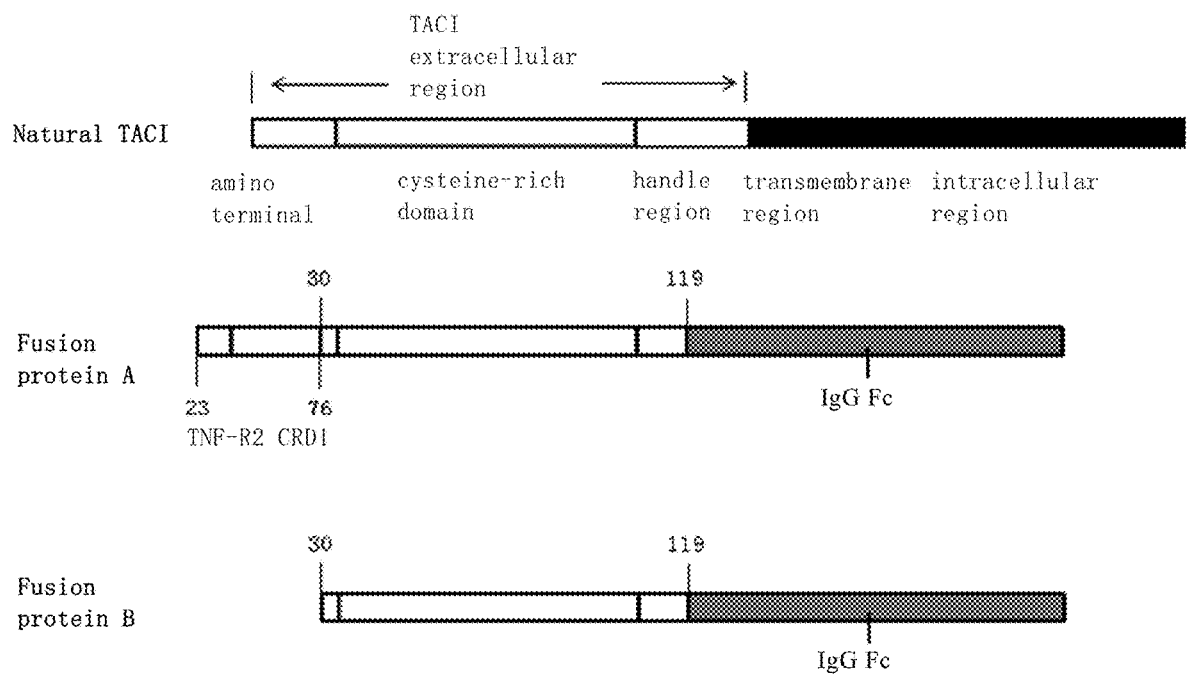
FIG. 3 shows the amino acid sequence of human wild type γ1 constant region Fc (SEQ ID NO.: 3). Hinge region, CH2 and CH3 regions are shown in the Figure. Since CH1 domain is not a part of Fc, it is not shown in this figure.
FIG. 4A shows a schematic structure of the fusion protein A and fusion protein B.

Fragment 3. Position 216-447 of human γ1 amino acid sequence, comprising a hinge region and two CH regions (FIG. 3).

Synthesis of cDNA of fragment 1.

PCR template was human cDNA prepared by a conventional method. 5'-end primer (AAGCTTGCGGCCGC-GAGCTCGGATCCACT (SEQ ID NO.: 6)) was a sequence of plasmid vector. To clone into pT vector, Not I enzyme cleavage site was introduced at 5'-end. 3'-end primer sequence was GGGGCAGGATCTCATAGCGTCACA-CACGGTGTCCGAG (SEQ ID NO.: 7), in which 19 TACI ribonucleotides were contained to link with TACI cDNA.

Synthesis of cDNA of fragments 2 and 3.

cDNA coding fragments 2 and 3 were already recombined in the vector encoding the fusion protein B (see Example 2). By using this vector as a template, 5'-end primer of fragment 2 and 3'-end primer of fragment 3 were used to amplify a recombinant gene coding fragments 2 and 3.

In order to link cDNA of fragment 1 with cDNA of fragments 2 and 3, the purified cDNAs of two fragments were mixed to act as template, 5'-end primer of fragment 1 and 3'-end primer of fragment 2/3 were used to carry out polymerase chain reaction. The amplified PCR fragment was purified, cloned into the vector of pCR-Blunt II-TOPO (purchased from Invitrogen). The recombinant plasmid was transfected into competent bacteria XL-1 (purchased from Invitrogen), the positive colonies were picked, and the recombinant plasmid was purified. The correct recombinant gene was identified by using enzyme digestion and sequencing.

The recombinant plasmid was cloned into a mammalian cell expression vector. The commercially available expression vector containing human CMV promoter and DHFR expression gene was used to screen stable cell lines expressing fusion protein and to amplify the copy number of expression gene. The recombinant plasmid and expression vector were digested with NotI and XbaI. The recombinant gene and vector after digestion were purified using gel purification method, linked in vitro and then transfected into competent bacteria DH5α (purchased from Invitrogen). The positive clones were picked up and TACI-Fc expression plasmid was amplified and purified.

Example 2

Construction of Plasmid Expressing Fusion Protein B

A precursor of the fusion protein B (FIG. 4) was composed of the following three parts from N-terminus to C-terminus, and the specific amino acid sequences were as follows.

Fragment 1. Human CD33 protein signal peptide containing the first 16 amino acids of N-terminal.

Fragment 2. Position 30-119 of TACI amino acid sequence, comprising two cysteine-rich domains and partial main stem sequence (FIG. 1).

Fragment 3. Position 216-447 of human IgG1 amino acid sequence, comprising a hinge region and two CH regions (FIG. 3).

The recombinant gene encoding fusion protein B was constructed by the overlapping polymerase chain reaction (PCR). Polymerase chain reaction (PCR) was carried out by using Plantium SuperMix (Invitrogen) according to the manufacturer's instructions. Each PCR fragment was purified by using gel purification kit for DNA fragment (Qiagen). Since TACI does not have protein secretion signal peptide, human CD33 protein secretion signal peptide was used in this example when the construction of the expression vector was carried out.

Synthesis of the gene coding CD33 protein secretion signal peptide. cDNA of this fragment was artificially synthesized: AGGTATAGCGGCCGCCACCATGCCGCT-GCTG CTACTGCTGCCCCTGCTGTGGGCAGGGGC-CCTGGCT (SEQ ID NO: 12). To clone into a mammalian cell expression vector, Not I enzyme cleavage site was introduced at 5'-end.

Synthesis of cDNA of fragment 2. PCR template was human cDNA prepared by a conventional method. 5'-end primer was GGCAGGGGCCCTGGCT GCTATGAGATCCTGCCCC(SEQIDNO.:8). The first 16 nucleotide sequence was the same as 3'-end sequence of CD33 encoding nucleotide in order to link PCR fragments of fragment 2 and fragment 1. 3'-end primer sequence was TGTAACAAGATTTGGGTTC CCTGAGCTCTGGTGGAAG(SEQIDNO.:9).

Synthesis of cDNA of fragment 3. PCR template was human cDNA prepared by a conventional method. The amplified DNA sequence encoded Position 216-447 of Fc amino acid sequence of human γ1 immunoglobulin. 5'-end primer was GAACCCAAATCTTGTTACA (SEQ ID NO.: 10) and complementary with 3'-end sequence of cDNA of fragment 2. 3'-end primer sequence was TGGTGGTG TCTAGAGAC TCATTTACCCGGAGACAGGGAGAGGC (SEQ ID NO.: 11). To clone into pT vector, Xba I enzyme cleavage site was introduced at 3'-end.

In order to link cDNAs of three fragments, the purified three fragments were mixed to act as template. 5'-end primer of fragment 1 (AGGTATAGCGGCCGCCACCATGC-CGCTGC (SEQ ID NO.: 13)) and 3'-end primer of fragment 3 (ibid., SEQ ID NO.: 11) were used to carry out polymerase chain reaction. The amplified PCR fragment was purified, cloned into the vector of pCR-Blunt II-TOPO (purchased from Invitrogen). The recombinant plasmid was transfected into competent bacteria XL-1 (purchased from Invitrogen), the positive colonies were picked up, and the recombinant plasmid was purified. The correct recombinant gene was identified by using enzyme digestion and sequencing.

The recombinant plasmid was cloned into a mammalian cell expression vector. The method was the same as that in Example 1. The recombinant plasmid expression vector was digested with NotI and XbaI. The recombinant gene and vector after digestion were purified by using gel purification method, linked in vitro and then transfected into competent bacterial DH5α (Invitrogen). The positive clones were picked up and TACI-Fc expression plasmid was amplified and purified.

Example 3

Construction of Fusion Protein Expression Cell Line

In this example, a CHO DG44 cell line for stable and high level of protein expression was established by a stable transfection and gene amplification method. The suspension cultivation of cloned CHO DG44 cells were carried out in serum-free and animal protein-free medium.

The original CHO DG44 cells were from Invitrogen company, and the cell culture and passage methods were based on the company's operating manual. The suspension cultivation of cells without being transfected were carried out in CD DG44 medium containing 8 mM Glutamine and 0.18% Fluronic F-18.

A plenty of expression plasmids encoding the fusion protein were prepared using Qiagen kit. The plasmids were purified by ethanol precipitation once so that the plasmids were not contaminated by bacteria. Before gene transfection, CD DG44 cells were passaged for three generations and then transfected. When the cell density reached $1 \times 10^6$/ml, 1 ml was taken and transferred onto 12-well culture plate, wherein each well was added with 1 ml.

Transfection was carried out by using transfection reagent LIPOFECTAMINE 2000 CD (Invitrogen). To obtain the highest transfection efficiency, three different ratios of plasmid with transfection reagent (1.5 μg:40 μl, 2 μg:40 μl and 3 μg:40 μl) were used to transfect each plasmid. Two days after transfection, cell culture solution was tested by Western Blot analysis (FIG. 5). The results showed that 2 μg of DNA plasmid had the highest transfection efficiency (FIG. 5, lane 3).

Cells transfected with 2 μg DNA plasmid were selected to use in the next screening step which was carried out in 96-well plates by limiting dilution method. The screening culture medium was CHO culture medium containing 20 nM or 100 nM methotrexate (MTX) without hypothanxin and thymidine. Two weeks later, the cell culture medium in each well was tested with ELISA method for detecting the fusion protein content and by SDS-PAGE for analyzing the protein in medium.

The results were shown in FIG. 6. The results showed that the genes encoding the fusion proteins A and B were integrated into the chromosome of the cell, and could express and secrete fusion proteins A and B, respectively, having a molecular weight of about 42 and 47 kDa, which were slightly higher than the theoretical values (about 5000 Da), and consistent with the predicted value (protein glycosylation phenomenon occurred when expressed in eukaryotic cells).

The cells expressing the fusion protein in high level were transferred to 24-well plate, cultured for 7 days followed by ELISA analysis to determine the protein content. From each fusion protein library, three high-expressing cells were selected for amplification and frozen.

Example 4

Preparation of Fusion Proteins

Cell lines expressing fusion protein A or fusion protein B were used as seed cells. The cells were cultured at the initial density of $0.5 \times 10^6$ cells/ml in S4 medium (containing 8 g/L glucose, 4 mmol/L glutamine and 0.5 mg/L insulin), wherein pH was 6.7-7.1, the dissolved oxygen was not less than 30% and the initial temperature was 35° C. When the cell density reached $6.5\text{-}7.0 \times 10^6$ cells/ml, the temperature was decreased to 31° C. On the next day, the temperature was decreased to 29° C. The concentration of sugar was maintained by supplementing glucose. When the cell survival rate was nearly 50%, the culturing was ended. The expression amount of the target protein of the fusion proteins A and B can reach 200 mg/L. Firstly, the cell culture medium was subjected to Protein A affinity chromatography. The purity of the target protein was 79.1% and the yield was 54.4%. Secondly, CM cation chromatography (the second step) was carried out. The purity of the target protein was 87.4% and the yield was 81.6%. Then Phenyl-650M hydrophobic interaction chromatography (the third step) was carried out. The purity of the target protein was 94.5% and the yield was 78.0%. Finally, ultrafiltration, concentration and liquid replacement were carried out. The purity of the target protein was 95.3% and the yield was 92.9%.

After four-steps of separation and purification, the non-reductive electrophoresis of the fusion proteins A and B was shown in FIG. 7.

Example 5

The Biological Activity of Fusion Protein A and Fusion Protein B on RPMI 8226 Cells The in vitro biological activity of TACI-Fc fusion protein is reflected by the inhibition effect on growth of human myeloma cells RPMI 8226 (purchased from ATCC) in the presence of dexamethasone and rhBAFF. Dexamethasone can induce RPMI 8226 cell apoptosis and decrease the experimental background, and BAFF can restore and promote cell growth. On this basis, TACI-Fc added to neutralize BAFF can weaken or even eliminate the promotion effect of BAFF on cell growth. The in vitro biological activity of TACI-Fc fusion protein can be detected by this method.

The reaction was carried out in 96-well cell culture plates. Each well was seeded with 10000 cells in 150 μl medium including 0.1 μM dexamethasone (Wako, CODE #041-18861) and 1 μg/ml rhBAFF (R&D, Cat #2149-BF/CF). The final concentrations of the samples for detection were a series of 4× gradient dilution with a starting concentration of 16 μg/ml. The rhBAFF-free experiment was used as a control. The plates were incubated at 37° C. carbon dioxide incubator for 5 days, 10 μl cck-8 solution (Cell Counting Kit-8, DOJINDO, cat: ck04) was added into each well for development. The color reaction was carried out at 37° C. for 6 hours and then the absorbance at 450 nm was detected using a microplate reader (Bio-Rad, iMark) with 655 nm as a reference. Because the sample to be detected could inhibit the cells by itself, the calibrated OD450 value was obtained by subtracting OD450 value of control group without rhBAFF from OD450 value of experimental group and then the graph was made based on calibrated OD450 value versus the logarithm of the concentration of the sample to be measured. The in vitro cell viability of the sample can be represented by $EC_{50}$, i.e., half effective inhibition concentration which was calculated by S-curve fitting using Origin software.

The results were shown in FIG. 8 showing a comparison of activity of fusion proteins A and B on RPMI 8226 cells. Each concentration effect curve showed that when the concentration of the fusion protein TACI-Fc was very low, rhBAFF in solution was substantially free state, thereby promoting growth and proliferation of RPMI 8226 cells. As the concentration of the fusion protein TACI-Fc gradually increased, rhBAFF was neutralized, free rhBAFF gradually decreased, and the cell proliferation decreased. When the amount of the fusion protein was sufficient to bind rhBAFF so as to completely counteract rhBAFF effect, the rate of cell growth decreased to minimum. It could be found from the graph of the absorbance at 450 nm versus the logarithmic of the sample concentration that the response curve of three factors appeared S-type. The calculated half effective inhibition concentration after fitting showed that the activity of the fusion protein A on RPMI 8226 cells was slightly lower than that of the fusion protein B.

Example 6

In Vitro Binding Assay Studies of Fusion Proteins A and B

In vitro binding assay studies of the fusion proteins A and B were performed mainly using ELISA principle. A certain amount of rhBAFF was fixed onto microtiter plates. Each well was added a series of gradient concentration of the fusion proteins A or B to conduct binding reaction. Finally, the amount of the fusion protein binding to rhBAFF on the plate was detected by HRP-conjugated anti-human Fc to examine the bind of rhBAFF.

The soluble fragments of the recombinant human BAFF were diluted with PBS (pH7.4) to 0.5 g/ml and then added to microtiter plates (Greiner bio-one, Cat #655001). Each well was added 50 μl and incubated at 4° C. overnight. On the next day, the plate was washed with ultrapure water and then blocked with 5% non-fat dried milk/PBST. The samples to be detected were diluted with 3-fold gradient starting from 3 μg/ml and then added to microtiter plates. Each well was added 50 μl of 0.8 μg/ml of detection antibody (Peroxidase-conjugated Goat anti-Human IgG, Fcγ Fragment Specific: Jackson ImmunoResearch LABORATORIES, INC. Code #109-036-098) and incubated for 1 hour at room temperature. PBST was used to wash again and then developing reaction was conducted. Each well was added 100 μl of 0.4 mg/ml OPD and the color development was conducted in the dark for 10 minutes. 100 μl of 1M $H_2SO_4$ was added to terminate the reaction. The absorbance at 490 nm was detected using a microplate reader (Bio-Rad, iMark) with 655 nm as the reference. The graph was made based on absorbance versus the logarithm of the molar concentration of the sample to be measured and $EC_{50}$ (the concentration corresponding to 50% of the absorption value change) was calculated by S-curve fitting using Origin software to represent the in vitro binding activity of the sample.

The results were shown in FIG. 9. As the concentration of the fusion protein added into each well of the microtiter plates increased, the bond of the fusion protein with rhBAFF fixed on the plate increased, and then more detection antibodies were bound, thereby obtaining higher absorbance at 490 nm from the color reaction. Both combination curves showed a typical S-curve characteristic. The calculated $EC_{50}$ after software fitting showed that $EC_{50}$ of the fusion protein A was slightly larger than that of the fusion protein B, indicating that the in vitro bond activity of the fusion protein A with rhBAFF was slightly lower than that of the fusion protein B.

Example 7

Pharmacokinetic Studies of the Fusion Proteins A and B in Animals

In order to study in vivo the pharmacokinetic characteristics of drugs, the relationship between blood concentration and administration time was determined. Forty-eight normal female BALB/C mice (18 to 20 g) were selected and seven time points were set up (namely, 1, 2, 4, 8, 24, 48 and 72 h) with 3 mice/time point. 5 mg/kg of fusion proteins A or B was separately administrated via intraperitoneal injection and the accurate administration time of each group was recorded. Then at each time point the mice were anesthetized with ether followed by removing the eyeball and drawing the blood. The serum was collected. ELISA was used to detect the blood concentration of two drugs at each time point.

As shown in FIG. 10, the fitting time curves of time and blood concentrations of two drugs were substantially similar. However, the blood concentration of the fusion protein A at different time point was significantly higher than that of the fusion protein B and was basically about 2 times. The in vivo half-lifes of the fusion proteins A and B in mice obtained through the software were 14 h and 11 h, respectively.

Example 8

In Vivo Pharmacodynamics Studies of the Fusion Proteins A and B in Normal Mice

The pharmacological effects of two drugs (fusion proteins A and B) on mice were evaluated in this example. Forty-two normal female BALB/C mice (18 to 20 g) were selected and divided into seven groups (6 mice/group), i.e., control group, the fusion protein A-5 mg/kg group, the fusion protein A-2.5 mg/kg group, the fusion protein A-1.25 mg/kg group, the fusion protein B-5 mg/kg group, the fusion protein B-2.5 mg/kg group, and the fusion protein B-1.25 mg/kg group.

On the first day, the blood was drawn from retinal venous plexus and the serum was collected. Then PBS was administered via intraperitoneal injection with different doses of the fusion proteins A and B (5 mg/kg, 2.5 mg/kg, 1.25 mg/kg). The drugs were administered every other day for two weeks. On 24 hours after the last administration, the mice were weighed and anesthetized with ether followed by drawing the blood from the canthus. After the mice were executed and dissected, the spleens were taken out and the peripheral tissues were removed. After slightly soaked up with filter paper, the spleens were weighed and the spleen weight/body weight was calculated. ELISA was used to detect the IgM concentration in serum of animals in each group before and after administration.

As shown in FIG. 11, the IgM concentrations in serum in the control group before and after administration had no significant difference. On day 14 after administration, the serum IgM concentrations using different doses of the fusion proteins A and B (5 mg/kg, 2.5 mg/kg, 1.25 mg/kg) were significantly decreased, and the difference between day 14 and day 0 was significant (** $p<0.01$). The fusion protein A group had no significant difference compared with the fusion protein B group.

As shown in FIG. 12, on day 14 after administration, the spleen weight/body weight in different doses of the fusion proteins A and B (5 mg/kg, 2.5 mg/kg, 1.25 mg/kg) groups were significantly decreased, wherein the fusion protein A (5 mg/kg, 2.5 mg/kg, 1.25 mg/kg) group and the fusion protein B (5 mg/kg, 2.5 mg/kg) group had significant difference when compared to the control group (**$p<0.01$ and *$p<0.05$). There was no statistically significant difference between the fusion protein B (1.25 mg/kg) group and the control group. The results showed that the effect of the fusion protein A on the reduction of spleen weight/body weight was significantly better than that of the fusion protein B.

Example 8

In Vivo Pharmacodynamics Studies of Fusion Proteins A and B in Asthma Model Mice In order to evaluate the pharmacological effects of two drugs (fusion proteins A and B) on asthma model mice, forty-four normal female C57/B6 mice (18 to 20 g) were selected and divided into seven groups for study, i.e., control group (6 mice), the model group (11 mice), the fusion protein A-5 mg/kg group (13 mice), and the fusion protein B-5 mg/kg group (14 mice). Firstly, on day 1 and day 14, OVA/ALUM suspension was injected intraperitoneally to sensitize the mice in the model group and experimental group. From day 13, PBS and different doses of the fusion proteins A and B were separately injected intraperitoneally every other day for 12 times. Then on day 28, day 30 and day 32, the mice were received the challenge from the nasal drop of OVA protein solution. Finally, 24 hours after administration was completed (i.e., day 36), the mice were weighed and anesthetized with ether followed by drawing the blood from the retinal vein plexus. After the mice were executed and dissected, the spleens were taken out and the peripheral tissues were removed. After slightly soaked up with filter paper, the spleens were weighed. The bronchoalveolar lavage fluid was extracted and the total number of leukocytes was calculated. ELISA was used to detect the serum IgE and IgM concentrations of mice in each group.

As shown in FIG. 13 (panel A), the serum IgM concentration in the model group on day 36 was significantly increased when compared with the control group. The IgM concentrations in the fusion protein A-5 mg/kg group and the fusion protein B-5 mg/kg group were significantly lower when compared with the model group ( $p<0.01$). As shown in FIG. 13 (panel B), the serum IgE concentrations in the model group, the fusion protein A-5 mg/kg group and the fusion protein B-5 mg/kg group on day 36 were increased to different level when compared with the control group, wherein there was significant difference between the IgE concentration of the fusion protein A group and that of the model group ($p<0.01$).

Surprisingly, compared with the fusion protein B, the fusion protein A could significantly reduce the IgE concentration indicating that the fusion protein A could more effectively inhibit the allergic reaction.

As shown in FIG. 14, the spleen weight/body weight of the model group on day 36 were increased significantly when compared with the control group. The spleen weight/body weight in the fusion protein A-5 mg/kg group and the fusion protein B-5 mg/kg group were significantly lower when compared with the model group (**$p<0.01$).

Example 9

Pharmaceutical Composition

According to the drug characteristics of the fusion proteins A and B, and taking the fusion protein A (40 mg/ml) as an example, several sets of pharmaceutical compositions were designed. The stabilities of aggregate and degradation of pharmaceutical compositions containing fusion protein A were investigated under the liquid accelerated test conditions, and the aggregate and degradation of the samples were analyzed by SEC-HPLC and SDS-PAGE method so that the pharmaceutical composition of the fusion protein A was ultimately determined.

A) buffer solution: 10 mM acetic acid buffer solution (pH5.0) containing 80 mg/mL trehalose;

B) buffer solution: 10 mM succinic acid buffer solution (pH5.0) containing 80 mg/mL sucrose;

C) buffer solution: 10 mM acetic acid buffer solution (pH5.0) containing 80 mg/mL trehalose and 0.05 mg/mL Tween 20;

D) buffer solution: 10 mM acetic acid buffer solution (pH5.0) containing 80 mg/mL trehalose and 0.05 mg/mL poloxamer 188;

E) buffer solution: 10 mM succinic acid buffer solution (pH5.0) containing 80 mg/mL trehalose and 0.05 mg/mL Tween 20;

F) buffer solution: 10 mM succinic acid buffer solution (pH5.0) containing 80 mg/mL trehalose and 0.05 mg/mL poloxamer 188.

Six groups of the pharmaceutical composition were stored at 4° C., 25° C. and 40° C. for 2 weeks. The stability results showed that after two weeks of storage at 4° C., none of the pharmaceutical compositions aggregated and degraded. After two weeks of storage at 25° C. and 40° C., the pharmaceutical compositions had no degradation fragments, but aggregate increased. The specific results were shown in Table 1.

TABLE 1

| Formulation | 25° C. | | 40° C. | |
|---|---|---|---|---|
| | 1 week | 2 week | 1 week | 2 week |
| A | 0.0% | 0.21% | 1.90% | 4.38% |
| B | 0.47% | 0.95% | 3.75% | 6.20% |
| C | 0.09% | 0.52% | 2.77% | 5.06% |
| D | 0.0% | 0.13% | 2.25% | 4.52% |
| E | 0.37% | 1.03% | 3.52% | 5.95% |
| F | 0.30% | 1.03% | 3.63% | 5.92% |

It could be seen from table 1 that in the pharmaceutical compositions A and D, the fusion protein A had a relatively high stability and was stable at 4° C. and 25° C. In the case of 40° C., the pharmaceutical composition D had a relatively higher tendency to aggregate than the pharmaceutical composition A. Therefore, for fusion protein A, a particularly preferred pharmaceutical composition was composed of 40 mg/mL fusion protein A, 80 mg/mL trehalose, and 10 mM acetic acid buffer solution (pH5.0).

Discussion

The extracellular region of tumor necrosis factor receptor (TNFR) superfamily usually contains 1 to 6 cysteine-rich structural domains (CRD) which are responsible for recognizing and binding to the ligand. These receptors are usually bound to the ligand in the form of trimer to exert the receptor functions. The above-mentioned functions are mediated by at least one cysteine-rich pre-ligand binding assembly domain (PLAD). More specifically, TNFR superfamily members, including TRAIL receptors 1, CD40, 60 kDa type TNFR and 80 kDa type TNFR, show the function of homo-association. The study has found that in the absence of ligand, PLAD is necessary and sufficient for formation of the receptor complex. Although PLAD is not directly involved in recognizing and binding to TNFα and TNFβ, the deletion of PLAD or mutation of PLAD may cause loss of the affinity capacity between the ligand and the receptor. Therefore, PLAD is relevant to the formation of TNFR complex and the bind of the ligand and plays a vital role in TNF-related signaling pathways.

The fusion proteins of the present invention can effectively block the PLAD region of TACI, thereby specifically inhibiting TACIR aggregation and terminating formation of TACI-BAFF complex so as to terminate the signal transduction.

The results also have shown that the TACI-FC fusion proteins of the present invention have an extended half-life of drug, can significantly reduce the IgE concentration in serum, and can effectively inhibit formation of TACI-BAFF complex, thereby terminating the signal transduction.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A fusion protein, which comprises:
   (a) an extracellular region of a TNF receptor, wherein the extracellular region comprises amino acids 23-76 of human TNF-R2;
   (b) an extracellular region of a BAFF receptor, wherein the extracellular region comprises amino acids 30-119 of human TACI; and
   (c) a human antibody Fc region;
   wherein (a), (b), and (c) are in the order of, from N-terminus to C-terminus, (a)-(b)-(c) or (b)-(a)-(c); and
   wherein the fusion protein inhibits the formation of a TACI-BAFF complex, and lowers the concentration of IgE in serum.

2. The fusion protein of claim 1, wherein (a) comprises an amino acid sequence selected from the group consisting of:
   (i) amino acids 23-76 of SEQ ID NO: 2,
   (ii) amino acids 23-118 of SEQ ID NO:2,
   (iii) amino acids 23-162 of SEQ ID NO:2, and
   (iv) amino acids 23-201 of SEQ ID NO:2.

3. The fusion protein of claim 1, wherein (b) comprises an amino acid sequence of amino acids 30-119 of SEQ ID NO:1.

4. The fusion protein of claim 1, wherein any two of (a), (b), and (c) are connected in a head-head, head-tail, or tail-tail manner.

5. A nucleic acid molecule which encodes the fusion protein of claim 1.

6. A vector comprising the nucleic acid molecule of claim 5.

7. A host cell comprising the vector of claim 6.

8. A method for producing a fusion protein, wherein the method comprises the steps of:

culturing the host cell of claim 7 under conditions suitable for expressing the fusion protein, thereby expressing the fusion protein; and
isolating or purifying the fusion protein.

9. A pharmaceutical composition which comprises the fusion protein of claim 1 and a pharmaceutically acceptable carrier.

10. A method for reducing IgE and/or IgM concentration in serum or blood of a subject in need thereof, the method comprising administering the fusion protein of claim 1 to said subject.

11. The method of claim 10, wherein the subject has asthma, systemic lupus erythematosus or rheumatoid arthritis.

12. The method of claim 10, wherein the subject has multiple myeloma, chronic lymphocytic leukemia, macroglobulinemia or plasma cell leukemia.

13. The fusion protein of claim 1, wherein the fusion protein comprises amino acids 39-398 of SEQ ID NO: 5, amino acids 23-398 of SEQ ID NO:5, or amino acids of 1-398 of SEQ ID NO: 5.

14. The fusion protein of claim 1, wherein in (c), the human antibody Fc region comprises amino acids 216-447 and is set forth in the amino acid sequence of SEQ ID NO:3.

15. The fusion protein of claim 1, wherein in (a), the human TNF-R2 amino acid sequence is set forth as SEQ ID NO:2.

16. The fusion protein of claim 1, wherein in (b), the human TACI amino acid sequence is set forth as SEQ ID NO:1.

17. The fusion protein of claim 15, wherein in (b), the human TACI amino acid sequence is set forth as SEQ ID NO:1.

\* \* \* \* \*

UNITED STATES PATENT AND TRADEMARK OFFICE
CERTIFICATE OF CORRECTION

| | | |
|---|---|---|
| PATENT NO. | : 10,562,954 B2 | Page 1 of 1 |
| APPLICATION NO. | : 15/310703 | |
| DATED | : February 18, 2020 | |
| INVENTOR(S) | : Zeling Cai et al. | |

It is certified that error appears in the above-identified patent and that said Letters Patent is hereby corrected as shown below:

On the Title Page

"(74) Attorney, Agent, or Firm – Wolf, Greenfield & Sack, P.C."
Should read:
--(74) Attorney, Agent, or Firm – Wolf, Greenfield & Sacks, P.C.--

Signed and Sealed this
Fifth Day of May, 2020

Andrei Iancu
*Director of the United States Patent and Trademark Office*

SEQUENCE LISTING

```
<160> NUMBER OF SEQ ID NOS: 13

<210> SEQ ID NO 1
<211> LENGTH: 293
<212> TYPE: PRT
<213> ORGANISM: Homo sapiens

<400> SEQUENCE: 1

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140
```

```
Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 2
<211> LENGTH: 461
<212> TYPE: PRT
<213> ORGANISM: Homo sapiens

<400> SEQUENCE: 2

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220
```

```
Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Gly Ala Gly Glu Ala Arg Ala Ser Thr Gly Ser Ser
                355                 360                 365

Asp Ser Ser Pro Gly Gly His Gly Thr Gln Val Asn Val Thr Cys Ile
370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Glu Lys Pro
                435                 440                 445

Leu Pro Leu Gly Val Pro Asp Ala Gly Met Lys Pro Ser
    450                 455                 460

<210> SEQ ID NO 3
<211> LENGTH: 232
<212> TYPE: PRT
<213> ORGANISM: Homo sapiens

<400> SEQUENCE: 3

Glu Pro Lys Ser Cys Tyr Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
```

130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 1197
<212> TYPE: DNA
<213> ORGANISM: Artificial sequence
<220> FEATURE:
<223> OTHER INFORMATION: Synthetic Polynucleotide

<400> SEQUENCE: 4
atggcgcccg tcgccgtctg ggccgcgctg gccgtcggac tggagctctg ggctgcggcg     60
cacgccttgc ccgcccaggt ggcatttaca ccctacgccc cggagccggg agcacatgc    120
cggctcagag aatactatga ccagacagct cagatgtgct gcagcaagtg ctcgccgggc    180
caacatgcaa agtcttctg taccaagacc tcggacaccg tgtgtgacgc tatgagatcc    240
tgccccgaag agcagtactg ggatcctctg ctgggtacct gcatgtcctg caaaaccatt    300
tgcaaccatc agagccagcg cacctgtgca gccttctgca ggtcactcag ctgccgcaag    360
gagcaaggca gttctatga ccatctcctg agggactgca tcagctgtgc ctccatctgt    420
ggacagcacc ctaagcaatg tgcatacttc tgtgagaaca agctcaggag cccagtgaac    480
cttccaccag agctcaggga acccaaatct tgttacaaaa ctcacacatg cccaccgtgc    540
ccagcacctg aactcctggg gggaccgtca gtcttcctct ccccccaaa acccaaggac    600
accctcatga tctcccggac ccctgaggtc acatgcgtgg tggtggacgt gagccacgaa    660
gaccctgagg tcaagttcaa ctggtacgtg acggcgtgg aggtgcataa tgccaagaca    720
aagccgcggg aggagcagta caacagcacg taccgtgtgg tcagcgtcct caccgtcctg    780
caccaggact ggctgaatgg caaggagtac aagtgcaagg tctccaacaa agccctccca    840
gcccccatcg agaaaaccat ctccaaagcc aaagggcagc ccgagaacc acaggtgtac    900
accctgcccc catcccggga tgagctgacc aagaaccagg tcagcctgac ctgcctggtc    960
aaaggcttct atcccagcga catcgccgtg gagtgggaga gcaatgggca gccggagaac   1020
aactacaaga ccacgcctcc cgtgctggac tccgacggct ccttcttcct ctacagcaag   1080
ctcaccgtgg acaagagcag gtggcagcag gggaacgtct tctcatgctc cgtgatgcat   1140
gaggctctgc acaaccacta cacgcagaag agcctctccc tgtctccggg taaatga     1197

<210> SEQ ID NO 5
<211> LENGTH: 398
<212> TYPE: PRT
<213> ORGANISM: Artificial sequence
<220> FEATURE:
<223> OTHER INFORMATION: Synthetic Polypeptide

<400> SEQUENCE: 5

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ala Met Arg Ser
65                  70                  75                  80

Cys Pro Glu Glu Gln Tyr Trp Asp Pro Leu Leu Gly Thr Cys Met Ser
                85                  90                  95

Cys Lys Thr Ile Cys Asn His Gln Ser Gln Arg Thr Cys Ala Ala Phe
            100                 105                 110

Cys Arg Ser Leu Ser Cys Arg Lys Glu Gln Gly Lys Phe Tyr Asp His
        115                 120                 125

Leu Leu Arg Asp Cys Ile Ser Cys Ala Ser Ile Cys Gly Gln His Pro
    130                 135                 140

Lys Gln Cys Ala Tyr Phe Cys Glu Asn Lys Leu Arg Ser Pro Val Asn
145                 150                 155                 160

Leu Pro Pro Glu Leu Arg Glu Pro Lys Ser Cys Tyr Lys Thr His Thr
                165                 170                 175

Cys Pro Pro Cys Pro Ala Pro Glu Leu Leu Gly Gly Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser His Glu Asp Pro Glu Val
    210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Lys Val Ser Asn Lys Ala Leu Pro Ala Pro Ile Glu Lys Thr Ile Ser
        275                 280                 285

Lys Ala Lys Gly Gln Pro Arg Glu Pro Gln Val Tyr Thr Leu Pro Pro
    290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350

Gly Ser Phe Phe Leu Tyr Ser Lys Leu Thr Val Asp Lys Ser Arg Trp
        355                 360                 365

Gln Gln Gly Asn Val Phe Ser Cys Ser Val Met His Glu Ala Leu His
    370                 375                 380

Asn His Tyr Thr Gln Lys Ser Leu Ser Leu Ser Pro Gly Lys
385                 390                 395

<210> SEQ ID NO 6
<211> LENGTH: 29

```
<212> TYPE: DNA
<213> ORGANISM: Artificial sequence
<220> FEATURE:
<223> OTHER INFORMATION: Synthetic Polynucleotide

<400> SEQUENCE: 6
aagcttgcgg ccgcgagctc ggatccact                                          29

<210> SEQ ID NO 7
<211> LENGTH: 37
<212> TYPE: DNA
<213> ORGANISM: Artificial sequence
<220> FEATURE:
<223> OTHER INFORMATION: Synthetic Polynucleotide

<400> SEQUENCE: 7
ggggcaggat ctcatagcgt cacacacggt gtccgag                                 37

<210> SEQ ID NO 8
<211> LENGTH: 34
<212> TYPE: DNA
<213> ORGANISM: Artificial sequence
<220> FEATURE:
<223> OTHER INFORMATION: Synthetic Polynucleotide

<400> SEQUENCE: 8
ggcaggggcc ctggctgcta tgagatcctg cccc                                    34

<210> SEQ ID NO 9
<211> LENGTH: 37
<212> TYPE: DNA
<213> ORGANISM: Artificial sequence
<220> FEATURE:
<223> OTHER INFORMATION: Synthetic Polynucleotide

<400> SEQUENCE: 9
tgtaacaaga tttgggttcc ctgagctctg gtggaag                                 37

<210> SEQ ID NO 10
<211> LENGTH: 19
<212> TYPE: DNA
<213> ORGANISM: Artificial sequence
<220> FEATURE:
<223> OTHER INFORMATION: Synthetic Polyonucleotide

<400> SEQUENCE: 10
gaacccaaat cttgttaca                                                     19

<210> SEQ ID NO 11
<211> LENGTH: 43
<212> TYPE: DNA
<213> ORGANISM: Artificial sequence
<220> FEATURE:
<223> OTHER INFORMATION: Synthetic Polynucleotide

<400> SEQUENCE: 11
tggtggtgtc tagagactca tttacccgga gacagggaga ggc                          43

<210> SEQ ID NO 12
<211> LENGTH: 67
<212> TYPE: DNA
<213> ORGANISM: Artificial sequence
<220> FEATURE:
<223> OTHER INFORMATION: Synthetic Polynucleotide

<400> SEQUENCE: 12
```

```
aggtatagcg gccgccacca tgccgctgct gctactgctg cccctgctgt gggcaggggc    60
cctggct                                                              67

<210> SEQ ID NO 13
<211> LENGTH: 29
<212> TYPE: DNA
<213> ORGANISM: Artificial sequence
<220> FEATURE:
<223> OTHER INFORMATION: Synthetic Polynucleotide

<400> SEQUENCE: 13
aggtatagcg gccgccacca tgccgctgc                                      29
```